(12) United States Patent
Tets et al.

(10) Patent No.: US 9,730,933 B2
(45) Date of Patent: *Aug. 15, 2017

(54) METHOD FOR TREATING LIVER DISEASES OF VARIOUS ORIGINS

(71) Applicants: Viktor Veniaminovich Tets, Saint-Petersburg (RU); Georgy Viktorovich Tets, Saint-Petersburg (RU)

(72) Inventors: Georgy Viktorovich Tets, Saint-Petersburg (RU); Viktor Veniaminovich Tets, Saint-Petersburg (RU); Konstantin Andreevich Krasnov, Saint-Petersburg (RU)

(73) Assignee: Viktor Veniaminovich Tets, Saint-Petersburg (RU)

( * ) Notice: Subject to any disclaimer, the term of this patent is extended or adjusted under 35 U.S.C. 154(b) by 0 days.

This patent is subject to a terminal disclaimer.

(21) Appl. No.: 15/154,633

(22) Filed: May 13, 2016

(65) Prior Publication Data

US 2016/0250214 A1 Sep. 1, 2016

Related U.S. Application Data

(62) Division of application No. 14/611,539, filed on Feb. 2, 2015, which is a division of application No. 13/382,626, filed as application No. PCT/RU2010/000291 on Jun. 4, 2010, now Pat. No. 8,962,640.

(51) Int. Cl.
*A61K 31/515* (2006.01)
*C07D 239/66* (2006.01)

(52) U.S. Cl.
CPC .......... *A61K 31/515* (2013.01); *C07D 239/66* (2013.01)

(58) Field of Classification Search
CPC ............................ A61K 31/505; A61K 31/515
See application file for complete search history.

(56) References Cited

U.S. PATENT DOCUMENTS

| | | | |
|---|---|---|---|
| 6,265,578 B1 | 7/2001 | Foley et al. | |
| 6,706,723 B2 | 3/2004 | Noe et al. | |
| 7,067,517 B2 | 6/2006 | Ebdrup et al. | |
| 7,279,470 B2 | 10/2007 | Ebdrup et al. | |
| 8,962,640 B2 * | 2/2015 | Tets | C07D 239/66 514/247 |
| 2005/0107414 A1 | 5/2005 | Noe | |
| 2012/0157483 A1 | 6/2012 | Tets et al. | |
| 2015/0158825 A1 * | 6/2015 | Tets | C07D 239/66 514/270 |

FOREIGN PATENT DOCUMENTS

| | | | |
|---|---|---|---|
| EP | 1043318 A1 * | 10/2000 | C07D 239/62 |
| RU | 1821209 C | 6/1993 | |
| RU | 2035906 C | 5/1995 | |
| RU | 2035906 C1 | 5/1995 | |
| RU | 2317981 | 2/2008 | |
| RU | 2400233 | 9/2010 | |
| WO | 9925699 A1 | 5/1999 | |
| WO | 00/47565 A1 | 8/2000 | |
| WO | 02/34726 A2 | 5/2002 | |
| WO | 2009059941 | 5/2009 | |

OTHER PUBLICATIONS

Tur-Kaspa et al., Alpha interferon suppresses hepatitis B virus enhancer activity and reduces viral gene transcription, J. Virol. Apr. 1990 vol. 64 No. 4 1821-1824.*
Beloborodova, E. et al., "Primenenie iodantipirina V lechenii khronicheskikh virusnykh gepatitov (Jodantipyrin Application in Treatment of Chronic Viral Hepatitis)" (2007), Retrieved from <URL: http://www.jodantipyrinsu/specialistiGepatitil201447> on Sep. 9, 2010 and May 7, 2014.
Chapter II Response to Written Opinion filed in PCT/RU2010/000291 accompanied by replacement sheets 3, 3-1, 3-2, 4, 5, 23, 23-1 of the specification (in Russian and English translation) and accompanying letter (in Russian and English translation) dated Apr. 6, 2011.
Franklin, "Induction of Rat Liver Drug-Metabolizing Enzymes by Heterocycle-Containing Mono-, Di-, Tri- and Tetra-arylmethanes" Biochemical Pharmacology, 1993, vol. 46, No. 4, pp. 683-689.
International Preliminary Report on Patentability dated Sep. 9, 2010, from corresponding International Application No. PCT/RU2010/000291.
International Search Report dated Oct. 28, 2010, from corresponding International Application No. PCT/RU2010/000291.
Jaeschke, et al., "Mechanisms of Hepatotoxicity" Toxicological Sciences, 2002, Vo. 65, pp. 166-176.
Lemasters, et al., "The mitochondrial permeability transition in cell death: a common mechanism in necrosis, and autophagy" Biochimica et Biophysica Acta, 1998, vol. 1366, pp. 177-196.
Machida et al., "Hepatitis C Virus Triggers Mitochondria! Permeability Transition with Production of Reactive Species, Leading to DNA Damage and STAT3 Activation" Journal of Virology, 2006, pp. 7199-7207.
Moskvin, et al., "Issledovanie azolov i azinov. SV. 5, 5'-Arilmetilenbis-(2-tiobarbiturovye) kisloty i ikh piridinievye soli (Azoles and Azines. CV.* 5,5-Arylmethylenebis(2-thiobarbituric) Acids and Their Pyridinium Salts)" 1998, Russian Journal of General Chemistry, vol. 68, No. 5, pp. 801-805, Translated from Zhurnal Obshchei Khimii, vol. 68, No. 5, 1998, pp. 848-852.

(Continued)

*Primary Examiner* — Erich A Leeser
(74) *Attorney, Agent, or Firm* — Troutman Sanders LLP

(57) ABSTRACT

The invention relates to medicine, in particular to gastroenterology, and lies in the field of treatment of liver diseases of various origins. For this purpose, the hepatoprotective agent that is introduced to the patient is embodied as derivatives of bis(2-thio-4,6-dioxo-1,2,3,4,5,6-hexahydropyrimidine-5-yl)arylmethanes. The method provides reduction of the manifestations of cytolysis under the influence of damaging agents and a statistically significant reduction of dysproteinemia, it accelerates restoration of detoxifying processes of the liver, increases induction of endogenic interferon alfa and, consequently, makes the protection of liver cells during hepatitides of various origins more effective.

5 Claims, No Drawings

(56) References Cited

OTHER PUBLICATIONS

Okovity, S.V., "Clinical Pharmacology Hepatoprotectors (Klinicheskaya farmakologiya gepatoprotektorov)" 2002, Pharmaindex Practic, Iss. 3, Retrieved from <URL: http://www.pharmindex.ru/practic/3_hepat.html> on Sep. 8, 2010 and May 7, 2014, p. 1-10.
Osipova et al., "Vegetable hepatoprotectors (Liv. 52) scheme of treatment of chronic hepatitis", Russian Medical Journal, 2005, 7, No. 1.
Russian Search Report dated Mar. 15, 2010, which issued during prosecution of Russian Patent Application No. which corresponds to the present application.
Written Opinion of the International Searching Authority dated Oct. 28, 2010, from corresponding International Application No. PCT/RU2010/000291.
Hudkins, et al., "Prodrug Esters of the Indolocarbazole CEP-751 (KT-6587)" Bioorganic & Medicinal Chemistry Letters,1998, pp. 1873-1876.
Van Sickle et al., "Inhibition of Cholesterol Synthesis by Cyclopropylamine Derivatives of Squalene in Human Hepatoblastoma Cells in Culture" Lipids, 1992, 27(3):157-160.
Tur-Kaspa et al., "Alpha interferon suppresses hepatitis B virus enhancer activity and reduces viral gene transcription" J. Virol. 1990, 64(4):1821-1824.
Jursic, Branko S. et al., "Preparation of 5,5'-pyrilidene and 5,5'-quinolidene bis-barbituric acid derivatives", Journal of Heterocyclic Chemistry, (2003), vol. 40, No. 03, pp. 465-474.

\* cited by examiner

METHOD FOR TREATING LIVER DISEASES OF VARIOUS ORIGINS

CROSS-REFERENCE TO RELATED APPLICATIONS

This application is a Divisional of U.S. application Ser. No. 14/611,539, filed on Feb. 2, 2015, which is a Divisional of U.S. patent application Ser. No. 13/382,626 filed Jan. 6, 2012, which issued as U.S. Pat. No. 8,962,640, which is U.S. National Phase Application under 35 U.S.C. §371 of International Patent Application No. PCT/RU2010/000291 filed Jun. 4, 2010 and claims priority from Russian Patent Application No. 2009126442 filed Jul. 7, 2009. The International Application was published on Jan. 13, 2011, as International Publication No. WO 2011/005142 A1 under PCT Article 21(2). The entire contents of all of these applications are hereby incorporated by reference.

TECHNICAL FIELD

The invention relates to medicine and can be used for treating liver diseases of various origins.

BACKGROUND ART

Known methods of treating liver diseases introduce into the organism organic hepatoprotective agents of natural or synthetic origin, e.g. "Essentiale", active ingredient—Phospholipids Essential (http://essenciale.lek-va.ru/), enter liver cells, invade membranes of hepatocytes, normalize to a certain extent the functioning of the liver and the metabolism of lipids and proteins, improve regeneration and slow down the formation of connective tissue in the liver.

Another method of treating liver diseases that comprises introduction of prostenon (synthetic PGE2) is more effective, see RU 1821209 A1.

As compared to the previously mentioned method, this method accelerates remission, demonstrates more effective results in reducing such manifestations of the disease as weakness, increased fatigue, a feeling of heaviness in the right hypochondrium, hyperalaninaemia, hyperbilirubinemia, elevated indicators of alkaline phosphatase and thymol test, blood levels of albumens, gamma globulins, immunoglobulins A and G, and cortisol; it helps regulate the upset balance between T helpers and T suppressors, and lower the level of protein-bound oxyproline in blood.

The main disadvantage of this method consists in that it cannot be used in the presence of a fairly broad spectrum of associated diseases that constitute a contraindication for prescription of prostaglandins E: pathology of genital sphere in women, hypotension, diarrhea of various etiologies, lid diseases, allergies etc.

Another known method for treating liver diseases of various origins also introduces a hepatoprotective agent, and in order to increase the effectiveness of the treatment the method uses an agent (hereinafter referred to as TDAA) that comprises tris-[N-(2,3-dimethylphenyl) anthranilate] aluminium, milk sugar, starch, low-molecular polyvinylpyrrolidone, Tween 80, Aerosil A-380 and calcium stearate at the following ratio of components, mass %:

| | |
|---|---|
| tris-[N-(2,3-dimethylphenyl) anthranilate] aluminium | 45.24-50.00 |
| Milk sugar | 4.52-5.0 |
| Starch | 39.21-43.36 |
| Polyvinylpyrrolidone | 3.39-3.75 |
| Tween 80 | 0.72-0.80 |
| Aerosil A-380 | 0.95-1.05 |
| Calcium stearate | 0.95-1.05, | see RU 2035906 C1.

This method has been taken as a prototype of the present invention.

Effectiveness and safety of the prototype method was tested on laboratory animals. The study showed that although the prototype has a certain hepatoprotective effect, the level of protection granted by implementation of the prototype method is relatively low; in addition, the prototype method has no directed influence upon the level of endogenic interferon alfa and, therefore, does not inactivate hepatitis viruses of various types, including the widely spreading hepatitis C virus.

SUMMARY OF THE INVENTION

It is a object of the present invention to provide a method for treating hepatitides of various origins that makes the protection of liver cells more effective and also provides specific antiviral activity implemented by inducing synthesis of own endogenic interferon alfa in the organism.

According to the inventive method for treating liver diseases of various origins by introducing a hepatoprotective agent, the hepatoprotective agent is embodied as derivatives of bis(2-thio-4,6-dioxo-1,2,3,4,5,6-hexahydropyrimidine-5-yl) arylmethanes.

The applicant has not found any sources of information containing data on engineering solutions identical to this invention, which enables to conclude that the invention conforms to the criterion "Novelty" (N).

The applicant has not found any sources of information containing data on the influence of the features of the invention on the technical result produced by the invention, which enables to conclude that the invention conforms to the criterion "Inventive Step" (IS).

BRIEF DESCRIPTION OF THE DRAWINGS

The invention is further explained by way of detailed description of examples of its embodiments without reference to any drawings.

Preferred Embodiment

Derivatives of bis(2-thio-4,6-dioxo-1,2,3,4,5,6-hexahydropyrimidine-5-yl)arylmethanes have a common formula:

$$\left[\left(X=\begin{array}{c}H\\N\\ \\N\\H\end{array}\begin{array}{c}O\\ \\ \\O\end{array}\right)_2\!\!\!\!\!\!\!\!\!\!\!\!\!CH\!\!-\!\!\!\begin{array}{c}R_1\\ \\ \\ \end{array}\!\!\!\!-R_2\right]^{2-} 2\,Cat^+,$$

where: X is selected from the group containing OXYGEN and SULFUR, $R^1$ is selected from the group containing HYDROGEN and ALKOXY GROUP, $R^2$ is selected from the group containing NITRO GROUP, HYDROXY GROUP and ALKOXY GROUP, $Cat^+$ is selected from the group containing PROTON, PYRIDINIUM- or 2-HYDROXYETHYL-AMMONIUM-CATION.

The inventive method uses the following derivatives:

X=O, $Cat^+$-$H_3N^+CH_2CH_2OH$, $R^1$=H, $R^2$=$NO_2$ (I); 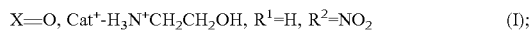

X=S, $Cat^+$-pyridinium, $R^1$=H, $R^2$=OH (II); 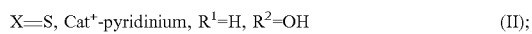

X=S, $Cat^+$-pyridinium, $R^1$=H, $R^2$=$NO_2$ (III); 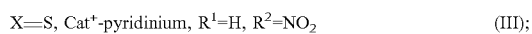

X=S, $Cat^+$-pyridinium, $R^1$=$R^2$=MeO (IV); 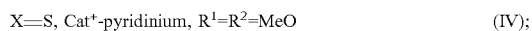

X=O, $Cat^+$-$H^+$, $R^1$=H, $R^2$=$NO_2$ (V). 

The substances used in the method are novel and are shown in Table 1.

Substances I-IV were obtained in the following way:

A mixture of 3 mmol of barbituric acid and 1.5 mmol of corresponding aldehyde in 10-15 ml of pyridine is boiled by means of reflux condenser during 1-2 h. After the reaction mass is cooled, the residue is filtered, washed by means of acetone and dried at 55-60° C. under residual pressure of 30 mmHg. In order to extract thio-derivatives from the reaction mass, 10-20 ml of dioxane or water are added to the reaction mass, the precipitated residue is filtered, washed by means of ethanol and dried. 3 mmol of barbituric acid and 1.5 mmol of corresponding aldehyde are used for conducting the reactions. In order to extract the products from the reaction mass, 10-20 ml of dioxane or water are added to the reaction mass, the precipitated residue is filtered, washed by means of ethanol and dried.

In order to obtain substance V, a solution of 0.5 g of benzaldehyde in 10 ml of ethanol is added to a mixture of 1 g of 2-thiobarbituric acid and 10 ml of ethanol. After stirring the reaction mass at 20° C. for 20-30 minutes, the residue is filtered and dried.

Table 2 below shows spectra of proton magnetic resonance of solutions of substances I-V in dimethylsulfoxide.

The inventive method is further explained by means of the provided examples.

The mechanisms of hepatoxicity—inflammation, cytolysis and cholestasis—are known to be universal and non-specific whatever the agent that induces liver damage [Frezza E. E. et al. Sex hormones and trace elements in rat $CCl_4$-induced cirrhosis and hepatocellular carcinoma.—European Journal of Cancer Prevention. 2(4), 357-359, 1993; Lin S. C. et al. Hepatoprotective effects of Taiwan folk medicine: Ixeris chinensis (Thunb.) Nak on experimental liver injuries.—American Journal of Chinese Medicine. 22(3-4), 243-54, 1994]. Therefore, damage to liver cells is similar for hepatitis caused by various bacteria, including those of *Leptospira* genus, chemical exposure at industrial facilities or as a result of poisonous substances that find their way into water or food products, as well as those caused by the effects of alcohol, certain medicines e.g. cytostatic drugs, exposure to radiation, and also various viruses (viruses of hepatitis A, E, B, D, C and some others that are not completely identified yet).

As for antiviral protection, it's worth mentioning that implementation of the inventive method causes an increase of the level of endogenous interferon alfa in human organism. Interferon alfa helps cells to defend against various viruses, including those that target liver cells (Hoofnagle, J. H., Di Bisceglie, A. M. (1997). The Treatment of Chronic Viral Hepatitis. *NEJM* 336: 347-356; Malaguarnera M., Di Fazio I., Ferlito L., Pistone G., Restuccia N., Trovato B.-A., Romano M. A comparison of four types of interferon alpha in the treatment of chronic hepatitis C. Curr Ther Res Clin Exp. 1998; 59(1): 48-59).

The inventive method was tested on 100 non-pedigree male rats weighting 250-270 g, using the easily available and reproducible model of toxic hepatitis. Animals were supplied by rat farm "Rappolovo", St. Petersburg, Russia.

All animals in the experiment, with the exception of the intact ones, received toxicant $CCl_4$ in the amount of 1.0 ml/kg in 50% solution of olive oil intragastrically (i/g) daily during 5 days through a non-traumatic feeding tube. After 5 days the presence of toxic hepatitis was confirmed by morphological image of liver, biochemical and functional indicators. After 24 hours after the last introduction of hepatotoxicant, the surviving rats were mass-randomized and divided into experimental groups. Animals from groups 3, 4 and 5 received known hepatoprotectors, while animals from groups 6-10 received substances shown in Table 1.

Group 1 - intact (n = 10);
Group 2 - $CCl_4$ (n = 10);
Group 3 - $CCl_4$ + Essentiale i/g, 100 mg/kg (n = 10);
Group 4 - $CCl_4$ + Carsil i/g, 100 mg/kg (n = 10);
Group 5 - $CCl_4$ + TDAA;
Group 6 - $CCl_4$ + substance I;
Group 7 - $CCl_4$ + substance II;
Group 8 - $CCl_4$ + substance III;  } 10 animals per each group
Group 9 - $CCl_4$ + substance IV;
Group 10 - $CCl_4$ + substance V.

Hepatoprotectors were introduced by way of treatment during 10 days in the following amounts: Essentiale—100 mg/kg; Carsil—100 mg/kg; prototype method—TDAA—100 mg/kg, the inventive method—substances I-V—50 mg/kg. Animals from group 2 instead of treatment received an equivalent volume of $CCl_4$. All substances were introduced intragastrically through a non-traumatic metal feeding tube.

A light starch suspension was used as a solvent.

Decapitation of rats was done under a light ether anesthesia, 5 and 10 days after the beginning of the experiment.

Differential diagnostics of the main illness syndromes was performed by evaluating the activity of hepatogenic enzymes in blood serum. Assessment of the degree of manifestation of cytolytic, cholestatic and mesenchymal inflammatory syndromes was performed by means of standard biochemical techniques with reagents "Bio-La-Test" by company "Lachema". During the study of the levels of indicator enzymes of the cytolytic syndrome, the activity of alanine aminotransferase (ALT), aspartate aminotransferase (AST), lactate dehydrogenase (LDH), γ-glutamyltransferase (γ-GT) and acid phosphatase (ACP) was evaluated. Excretory function of liver was also evaluated according to the content of bilirubin and the activity of excretory enzyme—marker of cholestasis of alkaline phosphatase (ALP). The content of lipids in blood was determined by evaluating the level of cholesterol and total lipids, dysproteinemia was assessed according to the level of total protein and by means of the thymol test

[1. Practical guidelines for studying hepatoprotective activity of pharmaceutical substances. From the book: Instructions for experimental (non-clinical) study of new pharmaceutical substances. Moscow, Russia—Remedium. 2000, pp. 228-231; 2. Laboratory research methods in clinical practice. Reference book, under the editorship of V. V. Menshikov. Moscow, Russia—Meditsina, 1987, 365 p.].

Lipid peroxidation and the activity of antioxidant system of liver were evaluated by the content of reduced glutathione in liver [Laboratory research methods in clinical practice. Reference book, under the editorship of V. V. Menshikov. Moscow, Russia—Meditsina, 1987, 365 p.] and the reserve of sulfhydryl groups in blood [Clinical evaluation of laboratory tests. Under the editorship of N. U. Tits, Moscow, Russia—Meditsina, 1986, 480 p. Kindsay R. H., Kitchin K. T., Sedlak J., Lindsay R. H. Estimation of total protein bound and nonprotein sulthydryl group in tissues with Ellman plangent. //Anal/biochem., 1968.-25(1-3).—p. 192-205].

Weight dynamics of the rats were determined by means of scales VLR-500.

In order to determine the relative mass of liver (ratio of liver mass in mg to body mass in g) of the animals, which characterizes the degree of manifestation of the inflammatory process in the organ, the liver was weighted using electronic scales 1602 MP by "Sartorius"

[A. I. Vengerovskiy, I. V. Markova, A. S. Soratikov Nonclinical study of hepatoprotectors. Guidelines. Journal of the pharmaceutical committee, 1999.—No. 2.—pp. 9-12].

During the hexenal sample the rats were given 80 mg/kg of hexenal intragastrically. The duration of anesthesia of the animals allows evaluating the rate of hexenal metabolism, which is performed by cytochrome P-450-dependent monooxygenase system of hepatocytes and characterizes the condition of antitoxic function of the liver

[A. I. Vengerovskiy, I. V. Markova, A. S. Soratikov Nonclinical study of hepatoprotectors. Guidelines. Journal of the pharmaceutical committee, 1999.—No. 2.—pp. 9-12; Clinical evaluation of laboratory tests. Under the editorship of N. U. Tits, Moscow, Russia—Meditsina, 1986, 480 p.; Kindsay R. H., Kitchin K. T., Sedlak J., Lindsay R. H. Estimation of total protein bound and nonprotein sulthydryl group in tissues with Ellman plangent. //Anal/biochem., 1968.-25(1-3). —p. 192-205; G. B. Kigel, A. V. Kharabadzhahyan Indicators of biological norm for laboratory animals. Rostov-on-Don, Russia, 1978, 95 p.].

Samples of blood and liver were taken from the animals after euthanasia by means of nembutal (pentobarbital) in the amount of 70 mg/kg.

In addition to the abovementioned parameters, the effectiveness of the treatment was assessed by clinical performance and survival rate of the animals.

Application of hepatoprotectors lowered mortality of animals in corresponding groups and significantly improved overall condition of rats, whereas the absence of treatment had a negative impact on the survival rate of the rats. Prior to death, rats had hemorrhagic rash around the nose, diarrhea and dramatic weight loss.

All surviving animals demonstrated low activity, their hair color had an icteritious hue.

Results of this study (mortality rate, clinical performance, biochemical and functional indicators), as well as the results of a histological study, allow to conclude that the introduction of $CCl_4$ created a model of a severe and moderately severe intoxication.

Survival rate in groups 2-10 by the end of introduction of $CCl_4$ and the hepatoprotectors (15 days) is shown in Table 3.

Since the indicators (including survival rate) in groups 6-10 are almost identical, column 6 of Table 3 etc. shows general (averaged and rounded off) indicators for animal groups 6-10.

Table 4 shows morphometric, biochemical and functional indicators of the condition of liver in subject animals during $CCl_4$ intoxication and during treatment according to the inventive method, in comparison with the methods of treatment by means of Essentiale and Carsil formulations, as well as the prototype method.

It is obvious from Table 4 that the inventive method for treatment of toxic lesion of liver that uses introduction of derivatives of bis(2-thio-4,6-dioxo-1,2,3,4,5,6-hexahydropyrimidine-5-yl)arylmethanes is much more effective than the known methods.

After the therapy treatment conducted according to the inventive method, manifestations of cytolysis in rats became significantly less pronounced. It was proved by the decrease of activity levels of indicator enzymes (ALT; AST; LDH, γ-GT, ACP) in blood serum as compared to the activity of the same enzymes in the group that did not receive any treatment. At the same time the treatment corrected the synthetic and pigment-forming functions of the liver, which was indicated by the increase of serumal content of total protein, total lipids and the decrease of content of total bilirubin. Results of the thymol test indicated a statistically significant reduction of dysproteinemia.

Cholestasis represents a substantial part of pathogenesis of liver lesions. Its intensity was evaluated on the basis of indicators of cholesterol, ALP and the level of bilirubin. All medicines reduced cholestasis, lowering the activity of ALP, reducing hyperbilirubinemia and hypercholesterolemia.

The observed positive changes of biochemical processes were accompanied by restoration of the detoxifying function of liver, which was manifested in a statistically significant reduction of duration of hexenal sleep in all subject groups that received hepatoprotectors. In addition, liver swelling was becoming smaller and the original weight of animals was gradually restoring. According to the obtained data, treatment removed the pro-oxidant effect of $CCl_4$, which manifested in a significant increase of the content of sulfhydryl groups and reduced glutathione.

Treatment improved overall condition of the animals: the rats became agile, their hair regained its original shine and color, animals started eating more.

Effectiveness of the inventive method is also confirmed by the results of histological studies. In rats under the influence of $CCl_4$ that received no treatment, the liver had persisting dystrophic alterations of hepatocytes in the form of diffuse liver steatosis. Hematoxylin and eosin staining showed indiscernible cell borders and vacuolization of cytoplasm. After implementation of the method according to the present invention the alterations of the hepatic framework were minimal and manifested only as small areas of proliferation of cellular elements.

In addition, interferon-inducing activity of the inventive method was studied. The study focused on the assessment of induction of interferon alfa in blood serum, which protects the organism against various viral infections (Hoofhagle, J. H., Di Bisceglie, A. M. (1997). The Treatment of Chronic Viral Hepatitis. *NEJM* 336: 347-356).

White non-pedigree mice weighting 18-22 g were used in the experiment. Medicines were homogenized in physiological saline solution with added Tween 80 and fed to the animals through a feeding tube in the amount of 0.2 ml. Animals had their blood samples taken 2, 4, 6, 8, 12 and 24 hours after the introduction of the medicine in order to assess its antiviral activity.

4 groups of animals were used, each group consisting of 10 animals.

1—Control group—received only solvents
2—Received Essentiale i/g
3—Received Carsil i/g
4—Received Cycloferon intraperitoneally
5—Prototype method
6—The inventive method The medicines were introduced in the following amount: Essentiale—100 mg/kg; Carsil—100 mg/kg; Cycloferon—100 mg/kg, prototype method—TDAA—100 mg/kg, the inventive method—50 mg/kg. Cycloferon was introduced intraperitoneally, while the other medicines were introduced intragastrically through a non-traumatic metal feeding tube. A light starch suspension was used as a solvent.

Cells of line L 929 were cultivated in 96-well plates, incubated at 37° C. for 24 hours with different amounts of animal serum. Virus of vesicular stomatitis (strain Indiana) in the amount of 100 CTD50 was introduced into the plate wells and incubated at 37° C. for 30-40 hours. After the incubation was completed the cells were washed with phosphate buffer, stained for 30 min by means of 0.1% solution of crystal violet in 30% ethanol, washed with physiological saline solution, air-dried and then the stain was extracted for 30 min by means of 30% solution of ethanol. The obtained solution was transferred to another plate, whereupon optical density in the wells was measured at wave length of 580 nm.

Protective effect of the blood serum was assessed by observing the reduction of manifestation of cytopathic effect of the vesicular stomatitis virus that could be observed from the increase of optical density in corresponding wells as compared to negative control wells. A titer of interferon was calculated as the reciprocal value of the highest dilution of serum that provided a statistically significant increase of the optical density in wells that was possible only with larger amount of preserved cells.

Data on antiviral protection of animal blood serum at various points in time after the introduction of the medicine are shown in Table 5.

The results indicate that the inventive method provided a statistically significant increase of antiviral protection of cells at all points in time after the introduction of the medicine. The fact that the Cycloferon started to take effect earlier is explained by its intraperitoneal introduction that allows the medicine to enter blood faster than a medicine introduced intragastrically according to the inventive method. However after 12 and 24 hours the cytoprotective action of the inventive method was 2-3 times stronger that the protective effect of the Cycloferon-based method. Introduction of Essentiale and Carsil, as well as the prototype method based on TDAA introduction, did not cause interferon to appear and did not protect the cells from the virus.

The level of antiviral protection depends on the time elapsed since the introduction of the medicine. The first spike of protective action takes place 2 hours after the introduction and is apparently caused by the formation of a complex in the serum (of the medicine or its metabolite on its own or together with serum proteins) that provides direct antiviral protection of cells. After the protective action decreases 4 hours after the introduction there is a increase of the level of antiviral activity caused by induction of endogenic interferon, which reaches its peak 8 hours after the introduction of the medicine, followed by a slow decline of the level of induced interferon, which nevertheless remains significantly above the control values up to 24 hours after the introduction.

Therefore, the inventive method increases the effectiveness of protection of liver cells during hepatitides of various origins.

INDUSTRIAL APPLICABILITY

The invention can be implemented by means of known materials and equipment. In applicant's opinion, this enables to conclude that the inventions conform to the criterion "Industrial Applicability" (IA).

TABLE 1

| No. | X | Cat | $R^1$ | $R^2$ | Name |
|---|---|---|---|---|---|
| I | O | $H_3N^+CH_2CH_2OH$ | H | $NO_2$ | 2-hydroxyethylammonium salt of bis(2-thio-4,6-dioxo-1,2,3,4,5,6-hexahydropyrimidine-5-yl)(4-nitrobenzyl)methane |
| II | S | $C_5H_5NH^+$ | H | OH | pyridinium salt of bis(2-thio-4,6-dioxo-1,2,3,4,5,6-hexahydropyrimidine-5-yl)(4-hydroxybenzyl)methane |
| III | S | $C_5H_5NH^+$ | H | $NO_2$ | pyridinium salt of bis(2-thio-4,6-dioxo-1,2,3,4,5,6-hexahydropyrimidine-5-yl)(4-nitrobenzyl)methane |
| IV | S | $C_5H_5NH^+$ | MeO | MeO | pyridinium salt of bis(2-thio-4,6-dioxo-1,2,3,4,5,6-hexahydropyrimidine-5-yl)(2,4-dimethoxybenzyl)methane |
| V | O | $H^+$ | H | $NO_2$ | bis(2-thio-4,6-dioxo-1,2,3,4,5,6-hexahydropyrimidine-5-yl)(4-nitrobenzyl)methane |

Spectra of proton nuclear magnetic resonance of solutions of substances I-V in dimethylsulfoxide

TABLE 2

| No. | $C^\alpha$ | Ar | Py | NH |
|---|---|---|---|---|
| I | 5.91 s | 6.82 d (2H, $H^{2,6}$), 7.47 d (2H, $H^{3,5}$), J8 Hz | 2.69 t (4H, $CH_2N$), 3.44 t (4H, $CH_2O$), J 5.4 Hz | — |
| II | 5.87 s | 6.55 d (2H, $H^{2,6}$), 6.77 d (2H, $H^{3,5}$), J 8.3 Hz | 7.65 m (4H. $H^{3,5}$), 8.10 m (2H, $H^4$), 8.71 m (4H, $H^{2,6}$) | 11.57 s |
| III | 6.06 s | 7.25 d (2H, $H^{2,6}$), 8.06 d (2H, $H^{3,5}$), J 8.5 Hz | 7.69 m (4H. $H^{3,5}$), 8.15 m (2H, $H^4$), 8.72 m (4H, $H^{2,6}$) | 11.72 s |
| IV | 5.85 s | 6.31 d (1H, $H^5$), 6.35 s (1H, $H^3$), 6.91 d (1H, $H^6$), J 8.4 Hz | 7.61 m (4H. $H^{3,5}$), 8.06 m (2H, $H^4$), 8.70 m (4H, $H^{2,6}$) | 11.47 s |
| V | 6.06 s | 7.26 d (2H, $H^{2,6}$), 8.07 d (2H, $H^{3,5}$), J 8.3 Hz | — | 11.69 s |

Survival rate in groups 2-10 by the end of introduction of $CCl_4$ and hepatoprotectors (15 days)

TABLE 3

| | $CCl_4$ intoxication | | | | |
|---|---|---|---|---|---|
| Indicators 1 | Group 2 (no treatment) 2 | Group 3 (Essentiale introduced) 3 | Group 4 (introduction of Carsil) 4 | Group 5 Prototype method (TDAA) 5 | Groups 6-10 The inventive method 6 |
| Survival rate (dead/total) | 4/10 | 2/10 | 3/10 | 3/10 | 1/10 |
| Survival rate (%) | 60% | 80% | 70% | 70% | 90% |

Morphometric, biochemical and functional indicators of condition of liver in subject animals during CCl₄ intoxication and during treatment according to the inventive method, in comparison with the methods of treatment by means of Essentiale and Carsil formulations, as well as the prototype method.

TABLE 4

| Indicators 1 | CCl$_4$ intoxication ||||||
|---|---|---|---|---|---|---|
| | Group 1 | Group 2 | Group 3 | Group 4 | Group 5 | Groups 6-10 |
| | 2 | 3 | 4 | 5 | 6 | 7 |
| Body weight, g | 261.4 | 201.4 | 224.0 | 217.2 | 206.3 | 227.2 |
| Relative liver mass, mg/100 g | 36.3 | 55.33 | 49.03 | 48.78 | 43.7 | 48.96 |
| Total protein, serum, g/l | 7.44 | 5.36 | 7.1 | 6.9 | 6.5 | 6.8 |
| Total lipids, serum, g/l | 3.5 | 2.5 | 3.4 | 3.2 | 2.9 | 3.3 |
| ALT, U/l | 124.2 | 726 | 378 | 398 | 450 | 410 |
| AST, U/l | 314 | 747 | 478 | 530 | 495 | 474 |
| LDH, mmol/h/l | 4.7 | 9.4 | 6.3 | 6.72 | 6.9 | 6.3 |
| γ-GT, U/l | 4.0 | 20.0 | 15.0 | 14.8 | 15.5 | 14.6 |
| ACP, μkat/l | 0.76 | 1.34 | 0.94 | 1.03 | 0.99 | 0.92 |
| ALP, μkat/l | 0.68 | 1.21 | 0.93 | 0.99 | 1.03 | 0.90 |
| Thymol test, turbidity units | 1.46 | 5.72 | 3.10 | 3.50 | 3.10 | 3.72 |
| Cholesterol, serum, mmol/l | 1.74 | 1.30 | 1.56 | 1.44 | 1.42 | 1.56 |
| Bilirubin, serum, μmol/l | 3.14 | 7.22 | 3.84 | 3.92 | 4.2 | 3.76 |
| SH-groups, serum, mg % | 1508 | 410 | 1062 | 1074 | 998 | 1084 |
| Reduced glutathione, mg % | 171 | 72 | 130 | 121 | 116 | 130 |
| Hexenal sleep, min | 25.9 | 89.40 | 31.40 | 41.50 | 40.0 | 30.6 |

Data on antiviral protection of animal blood serum at various points in time after the introduction of the medicine

TABLE 5

| | Interferon titer after X hours after the introduction of the medicine, h |||||| |
|---|---|---|---|---|---|---|
| Medicine | 2 hours | 4 hours | 6 hours | 8 hours | 12 hours | 24 hours |
| Control group | 5 | 5 | 5 | 5 | 5 | 5 |
| Essentiale | 5 | 5 | 5 | 5 | 5 | 5 |
| Carsil | 5 | 5 | 5 | 5 | 5 | 5 |
| Cycloferon | 90 | 18 | 110 | 125 | 35 | 22 |
| Prototype (TDAA) | 5 | 5 | 5 | 5 | 5 | 5 |
| The inventive method | 35 | 13 | 25 | 73 | 70 | 66 |

The invention claimed is:

1. A method of reducing liver damage in a subject in need thereof comprising administering to said subject a therapeutically effective amount of a compound of formula:

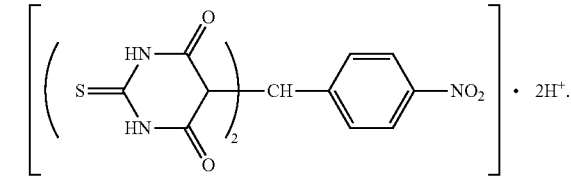

2. The method of claim 1, wherein the liver damage is caused by a chemical agent.

3. The method of claim 1, wherein the liver damage is caused by a bacterial infection.

4. The method of claim 1, wherein the liver damage is caused by radiation.

5. The method of claim 1, wherein the liver damage is caused by a viral infection.

* * * * *